US008323199B2

(12) United States Patent
Salcudean et al.

(10) Patent No.: US 8,323,199 B2
(45) Date of Patent: Dec. 4, 2012

(54) METHOD AND APPARATUS FOR IMAGING THE MECHANICAL PROPERTIES OF TISSUE FROM AN ENDOCAVITY

(75) Inventors: Septimiu Edmund Salcudean, Vancouver (CA); Reza Zahiri-Azar, Vancouver (CA); Danny French, Vancouver (CA); Xu Wen, Vancouver (CA)

(73) Assignee: The University of British Columbia, Vancouver (CA)

( * ) Notice: Subject to any disclaimer, the term of this patent is extended or adjusted under 35 U.S.C. 154(b) by 818 days.

(21) Appl. No.: 12/240,895

(22) Filed: Sep. 29, 2008

(65) Prior Publication Data

US 2009/0143679 A1 Jun. 4, 2009

Related U.S. Application Data

(60) Provisional application No. 60/960,433, filed on Sep. 28, 2007.

(51) Int. Cl.
*A61B 8/00* (2006.01)
*A61B 8/12* (2006.01)

(52) U.S. Cl. .................. 600/445; 600/444; 600/437

(58) Field of Classification Search .................. None
See application file for complete search history.

(56) References Cited

U.S. PATENT DOCUMENTS

| | | | |
|---|---|---|---|
| 4,494,548 A * | 1/1985 | Buon et al. | 600/446 |
| 4,979,952 A * | 12/1990 | Kubota et al. | 606/169 |
| 5,086,775 A | 2/1992 | Parker et al. | |
| 5,099,848 A | 3/1992 | Parker et al. | |
| 5,107,837 A | 4/1992 | Ophir et al. | |
| 5,107,844 A * | 4/1992 | Kami et al. | 600/463 |
| 5,125,410 A * | 6/1992 | Misono et al. | 600/463 |
| 5,178,147 A | 1/1993 | Ophir et al. | |
| 5,265,612 A | 11/1993 | Sarvazyan et al. | |
| 5,293,870 A | 3/1994 | Ophir et al. | |
| 5,454,371 A | 10/1995 | Fenster et al. | |
| 5,474,070 A | 12/1995 | Ophir et al. | |
| 5,497,776 A * | 3/1996 | Yamazaki et al. | 600/445 |
| 5,524,636 A | 6/1996 | Sarvazyan et al. | |
| 5,785,663 A * | 7/1998 | Sarvazyan | 600/587 |

(Continued)

OTHER PUBLICATIONS

Cespades, I., et al. "Methods for the estimation of subsample time-delays of digitized echo signals", Ultrasonic Imaging, 17:142-171, 1995.

(Continued)

*Primary Examiner* — Long V. Le
*Assistant Examiner* — Lawrence Laryea
(74) *Attorney, Agent, or Firm* — Jeffer Mangels Butler & Mitchell LLP

(57) ABSTRACT

The present invention relates to a method and apparatus for imaging the mechanical properties of a tissue region from within an endocavity of a patient. The apparatus generally comprises an ultrasound probe, a vibration assembly translationally coupled to probe and operable to vibrate the probe along a vibration plane, and a rotation assembly rotationally coupled to the vibration assembly and operable to rotate the probe and vibration assembly about a selected rotational range. The method generally comprises inserting an ultrasound probe into an endocavity of a patient, vibrating the probe along a vibration plane thereby causing deformational excitement of a tissue region contacted by the probe, capturing a first series of ultrasound images of the tissue region, rotating the vibration plane relative to the tissue region by a selected angular rotation, and capturing a second series of ultrasound images of the tissue region.

19 Claims, 7 Drawing Sheets

U.S. PATENT DOCUMENTS

| | | | |
|---|---|---|---|
| 5,839,441 A | 11/1998 | Steinberg | |
| 5,919,139 A | 7/1999 | Lin et al. | |
| 6,068,597 A | 5/2000 | Lin et al. | |
| 6,071,238 A * | 6/2000 | Chapelon et al. | 600/439 |
| 6,110,121 A * | 8/2000 | Lenker | 600/463 |
| 6,176,827 B1 | 1/2001 | Cohen-Bacrie et al. | |
| 6,270,459 B1 | 8/2001 | Konofagou et al. | |
| 6,508,768 B1 | 1/2003 | Hall et al. | |
| 6,514,204 B2 | 2/2003 | Alam et al. | |
| 6,558,324 B1 | 5/2003 | Von Behren et al. | |
| 6,569,108 B2 * | 5/2003 | Sarvazyan et al. | 600/587 |
| 6,592,526 B1 * | 7/2003 | Lenker | 600/463 |
| 6,679,845 B2 * | 1/2004 | Ritter et al. | 600/444 |
| 6,951,544 B2 | 10/2005 | Trahey et al. | |
| 7,052,462 B2 * | 5/2006 | Fukuda et al. | 600/445 |
| 7,162,065 B2 | 1/2007 | Ladak et al. | |
| 2005/0065426 A1 * | 3/2005 | Porat et al. | 600/407 |
| 2005/0119568 A1 | 6/2005 | Salcudean et al. | |
| 2006/0079782 A1 * | 4/2006 | Beach et al. | 600/450 |
| 2008/0161687 A1 * | 7/2008 | Suri et al. | 600/437 |

OTHER PUBLICATIONS

Cochlin, D.L., Ganatra, R.H., and Griffiths, D.F. "Elastrography in the detection of prostatic cancer", Clinical Radiology, 57(11):1014-1020, 2002.

Emelianov, Stanislav, Y., "Prostate carcinoma detection using combined ultrasound, elasticity, and tissue strain-hardening imaging", Annual Report, Dec. 31, 2001-Dec. 30, 2002, <http://handle.dtic.mil/100.2/ADA419173>.

Klauser, A., et al. "Real-time elastography for prostate cancer detection", J. Urology, 171(4 Suppl.):477, 2004.

Krouskop, TA, et al. "Elastic moduli of breast and prostate tissues under compression", Ultrasonic Imaging, 20 (4):260-274, 1998.

Li, Yinbo, A. Patil and J.A. Hossack, "Combined elasticity and 3D imaging of the prostate", Ultrasonics Symposium, 2005 IEEE, 3(18-21), Sep. 2005, 1435-1438.

Ljung L. (1999). Nonparametric Time and Frequency Domain Methods. System Identification, Theory for the User (pp. 168-190). Prentice Hall, PTR, NJ.

Lorenz, A., et al. "A new system for the acquisition of ultrasonic multicompression strain images of the human prostate in vivo", IEEE Trans on Ultrason Ferroelect & Freq Contr., 46(5) S. 1147-1154, 1999.

Miyanaga, Naoto, et al. "Tissue elasticity imaging for diagnosis of prostate cancer: a preliminary report", Int J Urol, 13 (12): 1514-1518, 2006.

Pesavento, A., and Lorenz, A. "Real time strain imaging and in-vivo applications in prostate cancer", IEEE Ultrasonics Symposium, 1647-1652, 2001.

Salcudean, S., et al. "Viscoelasticity modeling of the prostate region using vibroelastography", Proc. MICCAI 2007.

Scholz, et al. "Vibrography during tumor neurosurgery", Ultrasound Med, 24:985-992, 2005.

Tsutsumi, Masakazu, et al. "The impact of real-time tissue elasticity imaging (elastography) on the detection of prostate cancer: clinicopathological analysis", Int J Clin Urol, 12:250-255, 2007.

Turgay E., et al. "Parameter identification of tissue lumped models based on sequences of ultrasonic strain images", Second international conference on the Ultrasonic Measurement and Imaging of Tissue Elasticity, Corpus Christi, Texas, USA, Oct. 12-15, 2003.

Turgay, E., et al. "Identifying mechanical properties of tissue by ultrasound strain imaging", Ultrasound in Medicine and Biology, 32(2):221-235, 2006.

Zahiri-Azar, R. and S. Salcudean, "Motion estimation in ultrasound images using time domain cross correlation with prior estimates", IEEE Transactions on Biomedical Imaging, 53(10): 1990-2000, Oct. 2006.

* cited by examiner

METHOD AND APPARATUS FOR IMAGING THE MECHANICAL PROPERTIES OF TISSUE FROM AN ENDOCAVITY

RELATED U.S. APPLICATIONS

This application claims the benefit of U.S. Patent Application No. 60/960,433, filed on Sep. 28, 2007, which is incorporated herein by reference in its entirety.

ACKNOWLEDGEMENT OF GOVERNMENT SUPPORT

This invention was made with Government support under grant R21 CA120232 awarded by the National Institutes of Health. The Government has certain rights in the

FIELD OF THE INVENTION

The present invention relates to diagnostic imaging generally, and measurement of the mechanical properties of tissue using an endocavity transducer specifically.

BACKGROUND OF THE INVENTION

The basis of medical imaging is the measurement of a property of tissue that varies with tissue composition. Medical images are formed by displaying intensities as a function of these properties measured at multiple locations in the body. Mechanical properties of tissue are important indicators of disease potential. Indeed, palpation techniques are commonly used by medical doctors to determine the potential for disease, for example, stiffer tissue regions that can be felt as harder objects can indicate the presence of cancer. This is the basis for a number of clinical examinations such as the digital rectal examination for prostate cancer or bimanual exam for ovarian cancer. However, a need for improved medical imaging of tissue exists.

SUMMARY OF THE PREFERRED EMBODIMENTS

According to one aspect of the invention, there is provided an apparatus for imaging the mechanical properties of a tissue region from within an endocavity of a patient. The apparatus comprises:
  (a) an ultrasound probe insertable inside the endocavity and having a distal end contactable against the tissue region to be imaged;
  (b) a vibration assembly translationally coupled to a proximal end of the probe and operable to vibrate the probe along a vibration plane parallel to the longitudinal axis of the probe; and
  (c) rotation assembly rotationally coupled to the vibration assembly and operable to rotate the probe and vibration assembly such that the vibration plane is rotated about a selected rotational range.

The apparatus can further comprise a translation assembly translationally coupled to the probe and operable to translate the probe along its longitudinal axis.

The apparatus can further comprise a vibrational assembly that is operable to vibrate the probe along a vibration axis in the vibration plane and perpendicular to the longitudinal axis of the probe.

The apparatus can further comprise a cam and follower assembly translationally coupling the vibration assembly to the probe, wherein the cam rotates about an axis perpendicular to the vibration axis. A probe holder can be provided to which the probe is removably mounted. The follower is thus a wheel rotationally coupled to the probe holder, and the cam is rotationally coupled to a motor of the vibration assembly. The cam can include a first circular cylinder having a longitudinal axis perpendicular to the vibration axis such that when the wheel contacts the first cylinder there is no vibration along the vibration plane, and an adjacent second circular cylinder having a longitudinal axis at an angle from the longitudinal axis of the first cylinder such that the amplitude of vibration along the vibration plane will vary depending on the position of the wheel along the second cylinder.

The vibration assembly can further comprise a probe cradle to which the vibration motor is mounted, and wherein the rotation assembly comprises a motor, a drive shaft coupled to the motor, and a drive gear coupled to the drive shaft and rotationally coupled to a driven gear fixed to the probe cradle.

The tissue region can comprise at least a portion of a prostate, and in which case the probe is an endo-rectal ultrasound probe.

According to another aspect of the invention, there is provided a method of imaging the mechanical properties of a tissue region from within an endocavity of a patient. The method comprises the steps of:
  (a) inserting an ultrasound probe into an endocavity of a patient and against a tissue region within the endocavity;
  (b) vibrating the probe along a vibration plane parallel to a longitudinal axis of the probe thereby causing deformational excitement of the tissue region contacted by the probe;
  (c) capturing a first series of ultrasound images of the tissue region;
  (d) rotating the vibration plane relative to the tissue region by a selected angular rotation; and
  (e) capturing a second series of ultrasound images of the tissue region.

Multiple images can be taken each at a different selected angular rotation, such that a set of captured images form a three dimensional representation of the tissue region.

The vibration of the probe can follow a planned trajectory. Also, the vibration of the probe can be a filtered white noise with specified amplitude and bandwidth. Optionally, the vibration of the probe can be sinusoidal with specified amplitude and frequency. The rotation of the vibration plane can also follow a planned trajectory.

According to yet another aspect of the invention, there is provided a method and apparatus for imaging the mechanical properties of a tissue region from within an endocavity of a patient. The method comprises inserting an ultrasound probe into an endocavity of a patient and against a tissue region within the endocavity; and taking an ultrasound image of the tissue region by vibrating the probe along a vibration plane parallel to a longitudinal axis of the probe thereby causing deformational excitement of the tissue region contacted by the probe. An apparatus for performing such method includes an ultrasound probe insertable inside the endocavity and having a distal end contactable against the tissue region to be imaged, and a first transducer extending longitudinally along the probe; and a vibration assembly translationally coupled to a proximal end of the probe and operable to vibrate the probe along a vibration plane parallel to the longitudinal axis of the probe.

DETAILED DESCRIPTION OF THE PREFERRED EMBODIMENTS

The embodiments described herein relate to a vibro-elastography image acquisition apparatus for the measurement of the mechanical properties of a tissue region in a patient using a transducer. Particularly, the embodiments relate to an apparatus having an ultrasound probe to image a prostate using dynamic elastography, and components which cause the probe to vibrate in a vibration plane that is parallel to the longitudinal axis of the probe, as well as components to cause the probe to rotate a selected angular rotation such that vibration plane is rotatable relative to the prostate. This enables multiple ultrasound elastography images to be taken of the prostate each with a unique angular rotation, thereby forming a set of images which collectively represent a three dimensional image of the prostate.

Figure 1:
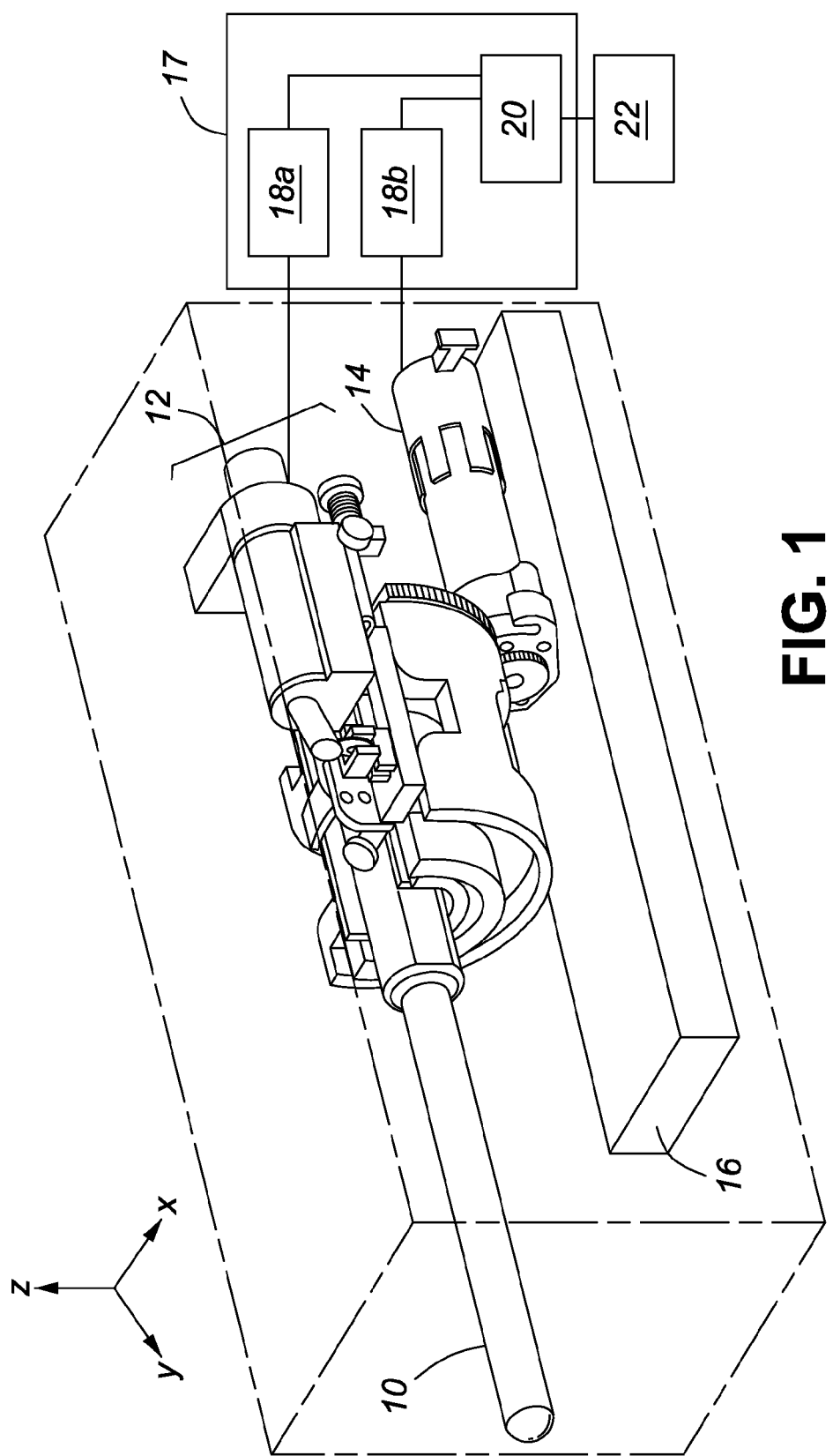
FIG. 1 is a perspective view of a vibro-elastography image acquisition apparatus for the measurement of the mechanical properties of a tissue region in a patient using an endocavity transducer, according to one embodiment of the invention.

Referring to FIG. 1, the image acquisition apparatus is shown generally as item 1 and comprises the following major components: an ultrasound probe 10, a vibration assembly 12, a rotation assembly 14, and a base 16 with an optional translation assembly (not shown). Also coupled to the apparatus 1 and shown in FIG. 1 is a control unit 17 and an ultrasound machine 22.

Using the base 16 as a reference to define a set of coordinate axes wherein the Y axis extends along the length of the base (and parallel to the probe 10), the X axis extends along the width of the base 16, and the Z axis extends along the height of the base 16, it can be seen in FIG. 1 that the vibration assembly 12 is translationally coupled to a proximal end of the probe 10 and is operable to vibrate the probe 10 along a vibration plane that is parallel to the longitudinal axis of the probe 10, i.e. along the Y axis. More particularly the vibration assembly 12 is operable to vibrate the probe 10 along a vibration axis in the vibration plane and perpendicular to the longitudinal axis of the probe 10. The rotation assembly 14 is rotationally coupled to the bottom of the vibration assembly 12, and is operable to rotate both the vibration assembly 12 and the probe 10 an angular range about an axis parallel to the Y axis. In FIG. 1, the apparatus 1 is shown with the rotation assembly 14 aligned at zero degrees so that the vibration plane is on the Y-Z plane and the vibration axis is the Z axis. The rotational assembly 14 in this embodiment is designed to allow rotation about ±90 degrees from this zero degree position. This enables the vibration axis to be rotated relative to a prostate (not shown) contacted by the probe 10. The optional translation assembly can be fixed to the base 16 and translationally coupled to the bottom of the rotation assembly 14 and is operable to move the rotation assembly 14, vibration assembly 12, and probe 10 back and forth in a direction parallel to the longitudinal axis of the probe 10, i.e. along the Y-axis.

The probe 10 is a cylindrical bi-plane endo-rectal ultrasound probe and has a longitudinal transducer (not shown) comprising a linear ultrasound imaging array extending inside the probe's housing from its distal end and along the longitudinal axis of the probe 10. This transducer serves to acquire ultrasound images in the sagittal and para-sagittal planes of a patient. The probe 10 also has a transverse transducer (not shown) comprising a convex ultrasound imaging array located inside the probe housing near the probe's distal end and along the transverse axis of the probe 10. This transverse transducer serves to acquire ultrasound images in the transverse plane of a patient.

The probe 10 is communicative with the ultrasound machine 22 and is operable to transmit captured images thereto. Suitable probes 10 are known in the art and may be for example a BK Medical Type 8658 or 8848 transducer, GE Healthcare ERB, or a Vermon TRT Biplane Endorectal transducer. In an alternative embodiment, the probe 10 may solely have an ultrasound imaging array along the longitudinal axis of the probe 10 or solely an ultrasound imaging array along the transverse axis of the probe 10. In a further alternative embodiment, the ultrasound transducer may have the ability to acquire simultaneous bi-plane or 3D images, such as the BK Medical Type 8808 transducer or Vermon tri-plane transducer.

Figure 2A:
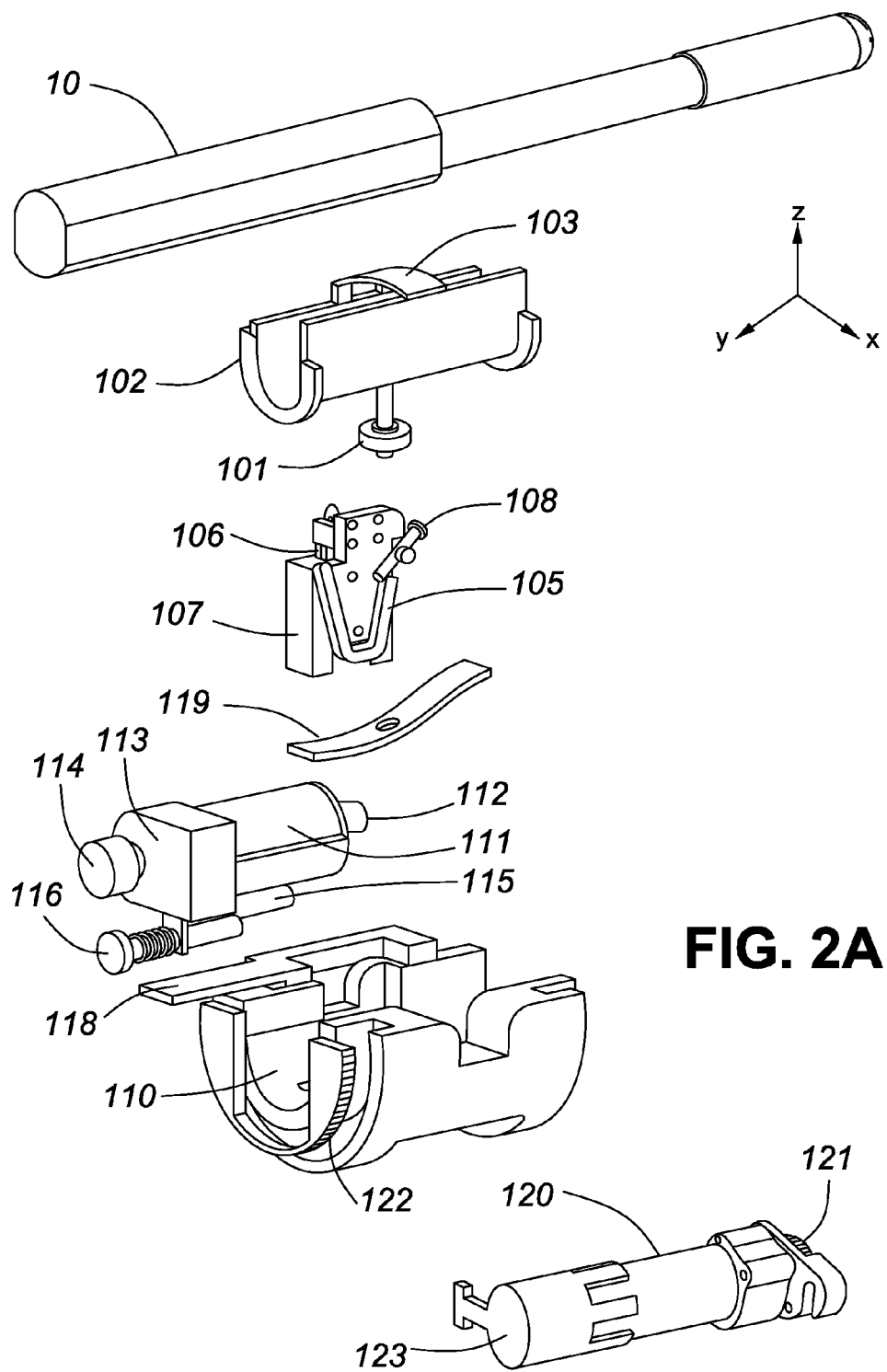
FIG. 2a is an exploded rear perspective view of some of the components of the vibro-elastography image acquisition apparatus shown in FIG. 1.

Referring to FIGS. 2(a) and (b), an exploded view is provided to show each of the components of the probe 10, vibration assembly 12 and the rotation assembly 14, as well as other components of the apparatus 1. The vibration assembly 12 comprises components 101 to 119 and the rotation assembly 14 comprises components 120 to 123, as are further described in the following paragraphs.

The vibration assembly 12 operates to vibrate the probe 10 along the vibration axis of the probe 10. In operation, this motion provides deformational excitation to the prostate allowing elasticity imaging of the prostate. The vibration assembly 12 generally comprises a probe holder assembly and a probe cradle assembly. The probe holder assembly has the probe 10 removably mounted thereto, and the probe cradle assembly is coupled to the base 16. A vibration motor 111 in the probe cradle assembly is rotationally coupled via a drive shaft to an eccentric cam 112 which in turn contacts a cam follower wheel 109 on the probe holder assembly. Rotation of the eccentric cam 112 thus causes the probe holder assembly and the probe 10 to oscillate, i.e. vibrate, relative to the probe cradle assembly and the rest of the apparatus 1.

The components of the probe holder assembly and the probe cradle assembly are described in more detail in the following paragraphs.

The probe 10 is removably mounted to the top surface of a probe holder 102 which is shaped as a semi-cylinder to snugly accept the contour of the probe 10. A lockable bracket 103 is rotatably coupled to one side of the probe holder 102 by means of a hinge (not shown), and removably coupled to a second side of the probe holder 102 by means of a thumbscrew (not shown). In a closed position, the lockable bracket 103 extends transversely across the concave side of the probe holder 102 securing the probe 10 within the probe holder 102. In an open position, the lockable bracket 103 extends outwardly from the probe holder 102 permitting the probe 10 to be removed from the probe holder 102.

The probe holder 102 also contains a triangular mounting plate 104 that is coupled to a matching triangular holder 105 by means of a locking screw 108. Extending downwards from the probe holder 102 is a stage slider 106 which slidably engages a mating stage base 107 mounted on a probe cradle 110 of the probe cradle assembly. Also on the probe holder is a wheel 109 rotatably mounted to the stage slider 106 and parallel to the drive shaft of motor 111.

It can be seen that the probe holder 102, mounting plate 104, triangular holder 105, stage slider 106, locking screw 108, and wheel 109 are all fixed relative to each other and to the probe 10. These components are reciprocatingly slidable relative to the rest of the vibration assembly 12 by way of the stage slider 106 being in slidable coupling with the stage base 107. It is this reciprocating sliding movement that provides the vibration along the vibration axis of the vibration assembly 12.

The vibration motor 111 has a cam 112 mounted on the distal end of its drive shaft. The vibration motor 111 is known in the art and can be for example a Maxon RE-25 Model 118755 motor. The cam 112 comprises: 1) a first circular cylinder having a longitudinal axis perpendicular to the vibration axis and parallel to the axis of the motor drive shaft; and 2) an adjacent second circular cylinder having a longitudinal axis at an angle of between 10 and 20 degrees from the longitudinal axis of the first cylinder and motor drive shaft.

A vibration encoder 113 is mounted at the opposite end of the shaft of the vibration motor 111 along with a knob 114 that permits the manual rotation of the shaft about the motor axis. The encoder 113 is known in the art and can be for example a US Digital E2-1000 encoder. The vibration motor 111 is coupled to a sliding mount 115 that is in slidable surface contact with a slider rail 118 mounted with screws to the to the probe cradle 110. A captive screw 116 is coupled to the sliding mount 115 and engages with a nut 117 coupled to the probe cradle 110. By adjusting the screw 116, the vibration motor 111 can be translated along the slider rail 118 in an axial direction parallel to the longitudinal axis of the probe 10.

The vibration motor 111 is positioned such that the cam surface 112 contacts the wheel 109 of the probe holder assembly. A leaf spring 119 is coupled to the probe cradle 110 and is in surface contact with the bottom (convex end) of the probe holder 102. The leaf spring 119 pushes directly on the lower convex part of the probe holder 102 such that either (i) the wheel 109 is in contact with the cam 112, or (ii) the locking screw 101 of the probe holder 102 is against the bottom of the cradle 110. The leaf spring 119 applies a force to the probe holder assembly in a direction away from the probe cradle 110, such that the cam 112 is maintained in contact with the wheel 109 during normal operation of the apparatus 1.

Figure 3:
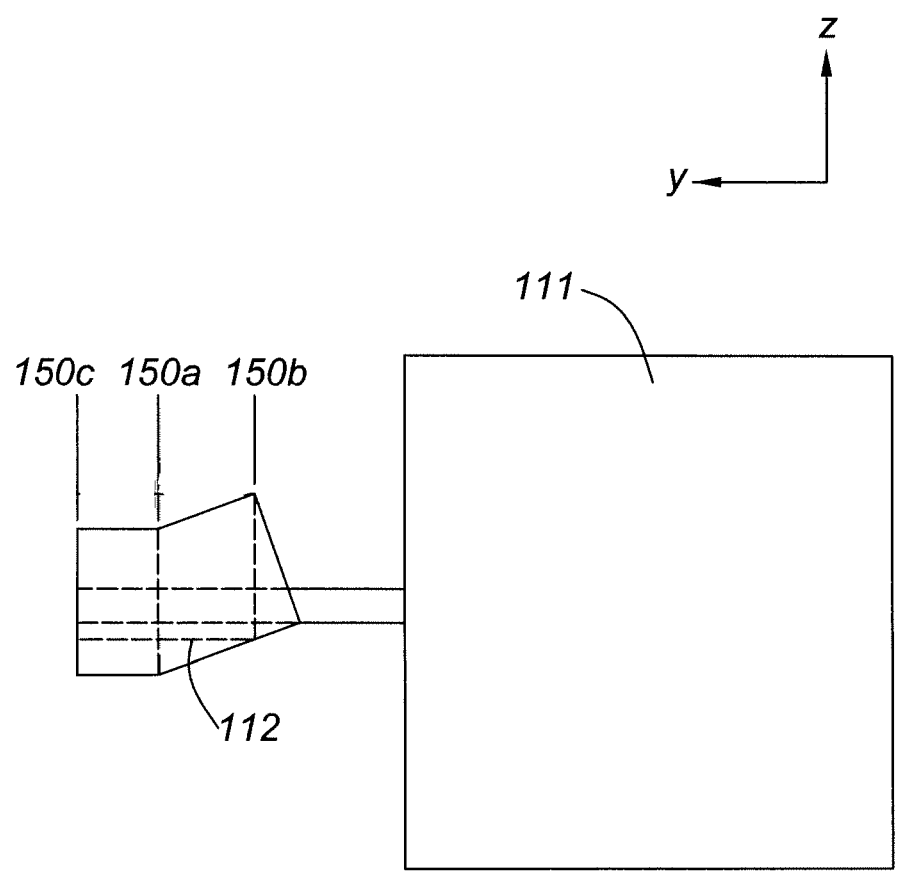
FIG. 3 is a representative drawing of a front view of a motor and cam forming part of a vibration assembly in the vibro-elastography image acquisition apparatus shown in FIG. 2.

Referring to FIG. 3, a front view is provided of the vibration motor 111 and the cam 112. Depending on the axial position of the vibration motor 111 (along the Y-axis), the wheel 109 will contact the cam 112 at a point between points 150b and 150c along the surface of the cam 112. Between points 150a and 150c along the surface of the cam 112, the wheel contacts the surface of the first cylinder of the cam 112, and since this surface is not eccentric, the probe holder assembly will not translate relative to the probe cradle assembly. However, when the wheel 109 moves away from point 150a to point 150b, the wheel 109 contacts surface of the second cylinder of the cam 112 which because of its eccentricity will cause the probe holder assembly to translate in reciprocating manner relative to the probe cradle assembly. The higher up the wheel 109 moves along the surface of the second cylinder of the cam 112, the greater the amplitude of the oscillation. The amplitude of oscillation of the probe holder assembly can be controlled by adjusting the screw 116 to select a desired position of the wheel 109 along the surfaces of the first and second cylinders of the cam 112.

Figure 2B:
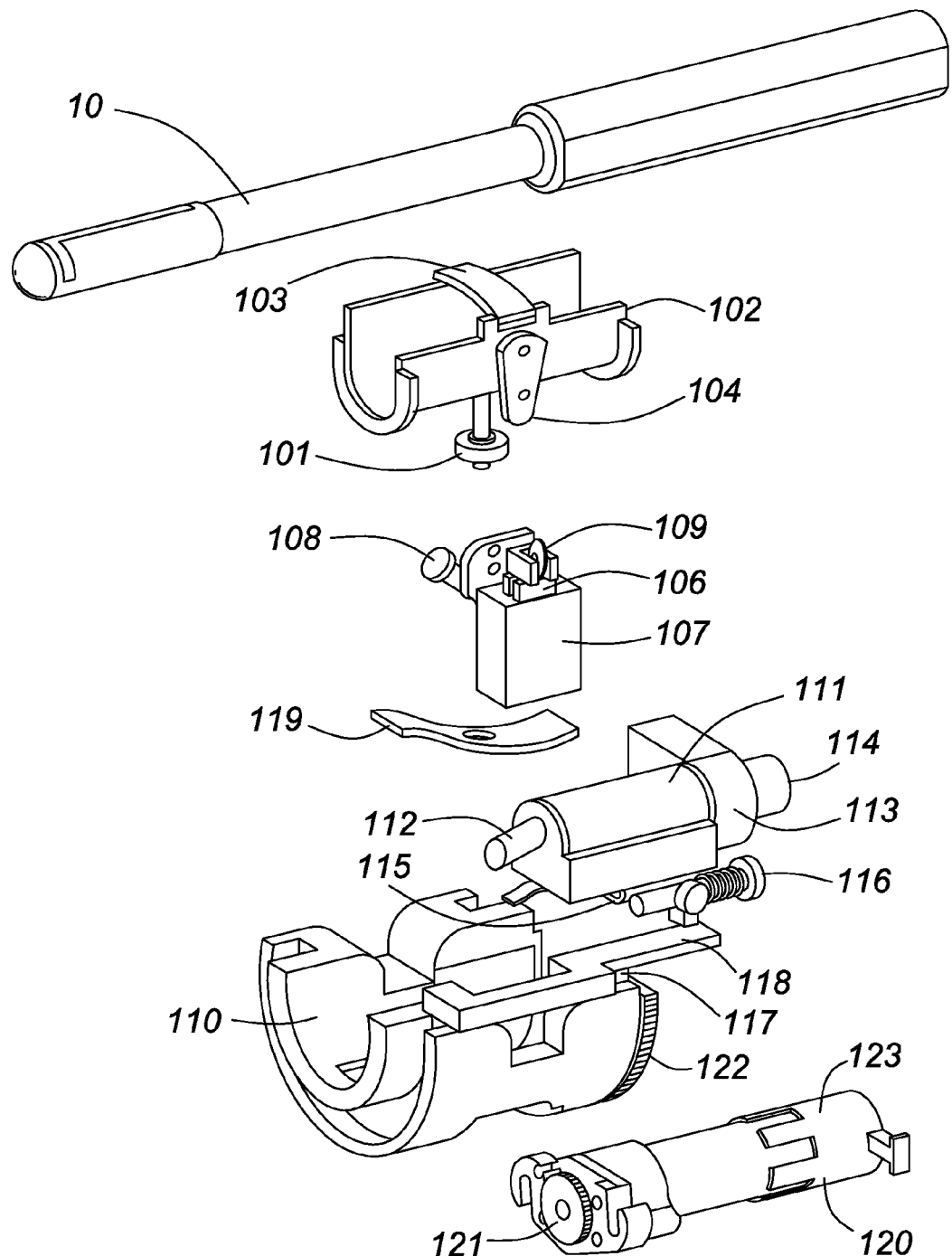
FIG. 2b is an exploded front perspective view of some of the components of the vibro-elastography image acquisition apparatus shown in FIG. 1.

Referring to FIG. 2, when vibration of the probe 10 is not desired, the probe 10 and probe mount assembly can be restricted from vibrational motion by locking the probe holder 102 against the probe cradle 110 by tightening a locking screw 101. The locking screw 101 comprises a threaded screw and a locking nut. The threaded screw is coupled to the bottom of the probe holder 102 and passes through holes (not shown) in the leaf spring 119 and the bottom of the probe cradle 110. The locking nut engages the threaded screw at the bottom of the probe cradle 110 and is operable to be tightened against the bottom surface of the probe cradle 110, thereby compressing the leaf spring 119 and locking the probe holder 102 against the probe cradle 110 in a predictable position.

Figure 4:
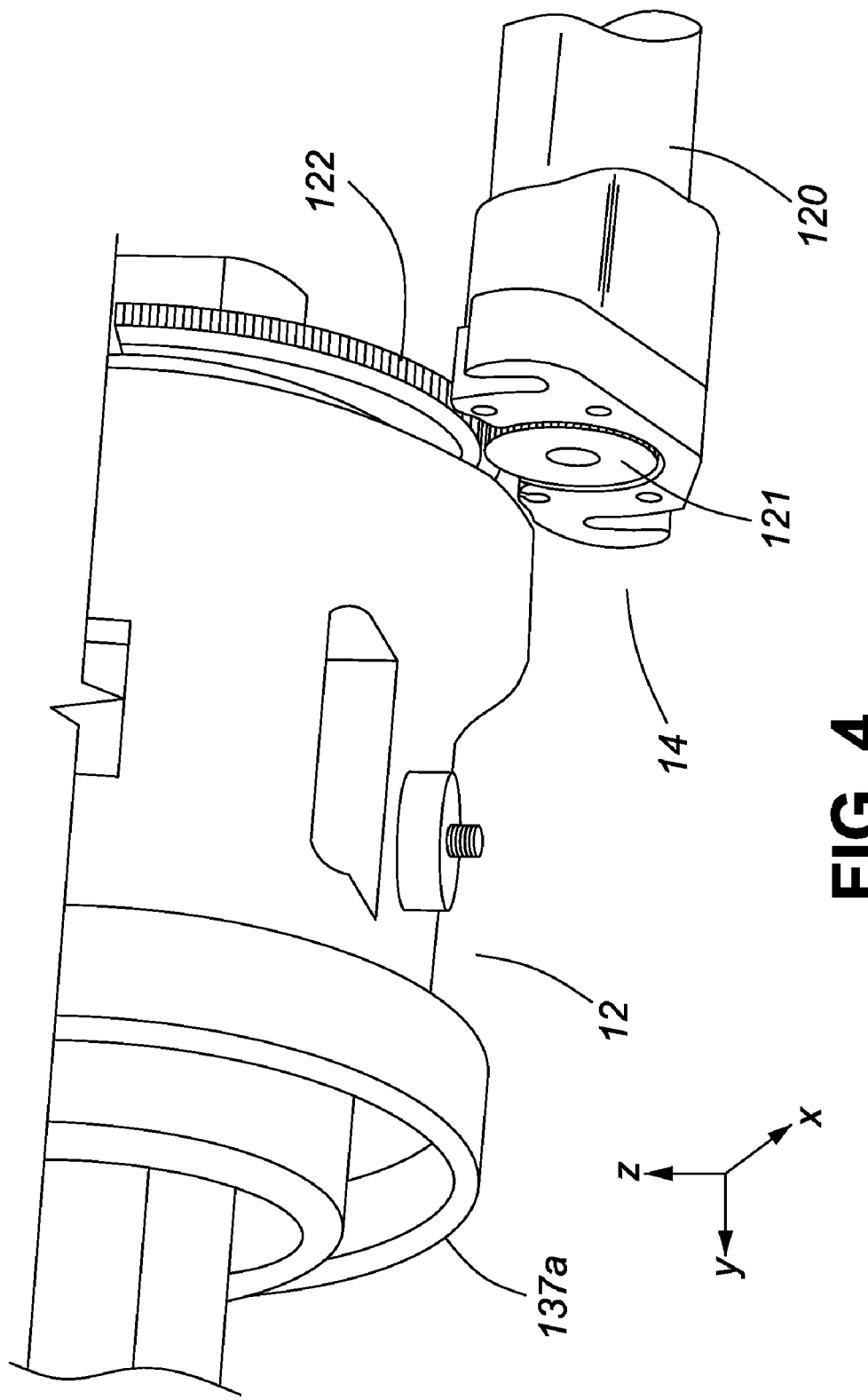
FIG. 4 is a front perspective view of a portion of a rotation assembly and the vibration assembly in the vibro-elastography image acquisition apparatus shown in FIG. 2.

Referring to FIG. 4, the rotation assembly 14 is shown comprising: a rotation motor 120, a rotation encoder 123 (not shown), a driving gear 121 coupled to the motor 120 via a drive shaft, and a driven gear 122 fixed to the probe cradle 110. The rotation assembly 14 operates to rotate the entire vibration assembly 12 about the longitudinal axis of the probe 10, i.e. parallel to the Y-axis. The rotation motor 120 is mounted to the base 16. The rotation motor 120 is known in the art and can be for example a Faulhaber 2342 motor with a 1/3.7 gear. The driving gear 121 is coupled to the rotation motor 120 at one end of its drive shaft, while the encoder 123 is coupled to the rotation motor 120 at the opposite end of its shaft.

The driven gear 122 is a semi-circular gear fixed to the rear of and in axial alignment with the probe cradle 110 and probe 10, i.e. parallel to the Y axis. The driven gear 122 is rotatably coupled to the driving gear 121, such that rotation of the driving gear 121 by the rotation motor 120 rotates the driven gear 122. Since the driven gear 122 is fixed to the probe cradle 110 forming part of the vibrational assembly 12, the rotation of the driven gear operates to rotate the entire vibration assembly 12 about the longitudinal axis of the probe 10. The angle of rotation of the vibration assembly 12 is measured by the encoder 123. The encoder 123 is known in the art and can be for example a standard IE2 integrated encoder with the Faulhaber 2342 motor mentioned above. The vibration assembly 12 may also be manually rotated by an operator by applying a rotational force to the vibration assembly 12.

In the present embodiment, the optional translation assembly is a standard CIVCO Medical Solutions EX II stepper onto which the probe cradle 110 is mounted. The motorized rotation of the probe cradle 110 is achieved by replacing the passive geared encoder used in the CIVCO EXII stepper to measure the probe rotation, with the driving gear 121, rotation motor 120 and rotation encoder 123. In the alternative, the CIVCO EXII stepper can be modified to include a translation motor and translation encoder, allowing the translational motion of the encoder probe 10, vibration assembly 12 and rotation assembly 14 to be controlled by the control unit 17.

Figure 5:
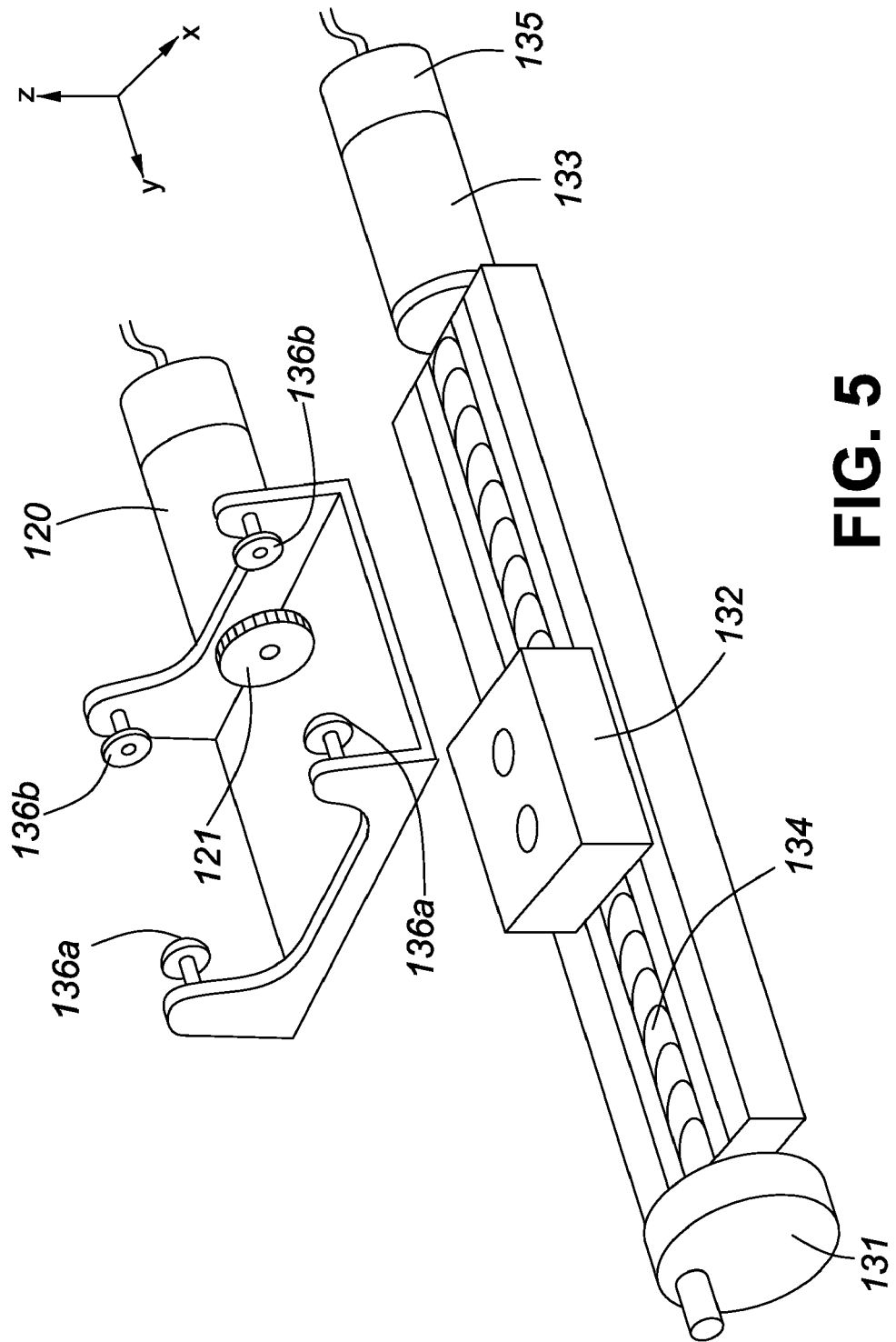
FIG. 5 is a schematic perspective view (exploded) of the translation assembly forming part of a vibration assembly in the vibro-elastography image acquisition apparatus shown in FIG. 2.

In the further alternative, and referring to FIG. 5, a motorized translation assembly 16 is provided comprising: a knob 131, a lead screw 134, a traveler 132, the base 16, a translation motor 133, a translation encoder 135, and two pairs of guide wheels 136a and 136b. The lead screw 134 is rotationally coupled to the base 130 resting in a channel along the length of the top surface of the base 130. The knob 131 is coupled to one end of the lead screw 134 and the shaft of the translation motor 133 is coupled to the opposite end of the lead screw 134, such that the lead screw 134 can be rotated about its longitudinal axis by the rotation of either the knob 131 or the translation motor 133. The translation motor 133 is known in the art and can be for example a Faulhaber 2342 motor with a 1/3.7 gear. The encoder 135 is also coupled to the shaft of the translation motor 133. The encoder 135 is known in the art and can be for example an integrated encoder IE2 with the Faulhaber 2342 motor mentioned above. The traveler 132 is coupled to the lead screw 134 such that rotation of the lead screw 134 will cause the traveler 132 to translate along the longitudinal axis of the lead screw 134. Circular guides 136a and 136b are coupled to the traveler 132 and contain metal rollers having rotational axes parallel to the longitudinal axis of the lead screw 134. The probe cradle 110 has matching channels 137a and 137b in which the guide wheels 136a and 136b fit, such that the probe cradle 110 rests on the metal rollers of the circular guides 136a and 136b such that the probe cradle 110 is rotatable about the longitudinal axis of the probe 10.

Referring to FIG. 1, the control unit 17 comprises microcontrollers 18a and 18b and controlling computer 20. Controlling computer 20 is communicative with microcontroller 18a and is operable to transmit desired vibrational characteristics of the probe 10 thereto. In the present embodiment, the vibrational characteristics comprise the amplitude and the frequency content of the vibrational motion of the probe 10. As described above, the maximum amplitude of vibration of the probe 10 is controlled by adjusting the point of contact of the wheel 109 on the cam 112. In one complete rotation of the shaft of the vibration motor 111, the probe mount assembly will travel this maximum amplitude. However, lower amplitudes of vibration can be achieved by rotating the shaft of the vibration motor 111 back and forth between angles of rotation less than 360 degrees. In this manner, microcontroller 18a is operable to control the rotation of the vibration motor 111 such that the vibrational amplitude of the probe 10 can be varied between zero and the maximum selected amplitude. In the alternative, the axial motion of the vibration motor 111 along the slide rail 118, and thus the amplitude of vibration, can be controlled by microcontroller 18a through a motorized stage. Microcontroller 18a is communicative with the vibration motor 111 and the vibration encoder 113, and is operative to control the vibrational characteristics of probe 10 by driving vibration motor 111 in response to information on the angular position of vibration motor 111 received from vibration encoder 113.

Controlling computer 20 is also communicative with microcontroller 18b and is operable to transmit desired rotational characteristics of the probe 10 thereto. In the present embodiment, the rotational characteristics comprise the angular range of motion and the motion duration of the probe 10 about the longitudinal axis of the probe 10. Microcontroller 18b is communicative with the rotation motor 120 and the rotation encoder 123, and is operative to control the rotational characteristics of probe 10 by driving rotation motor 120 in response to information on the angular position of rotation motor 120 received from rotation encoder 123.

The controlling computer 20 comprises a processor, a memory, a display, an input device, and a communication device. The memory stores a program which is an expression of the steps of the vibro-elastography image acquisition method described below. The processor executes the program to apply the vibro-elastography image acquisition method. The display displays a graphical user interface (GUI), as instructed by the processor executing the program, that permits a user to control the trajectory of the probe 10 in accordance with the vibro-elastography image acquisition method. The input device allows an operator to initiate and provide information required by the vibro-elastography image acquisition method. Suitable input devices are known in the art and can be for example a standard computer keyboard and computer mouse. The communication device permits the controlling computer 20 to communicate with microcontrollers 18a to 18b and ultrasound machine 22. The controlling computer 20 is operable to communicate desired vibrational characteristics and rotational characteristics to microcontrollers 18a and 18b, respectively. In addition, controlling computer 20 is operative to communicate actual vibrational and rotational characteristics to ultrasound machine 22 to allow for synchronized data collection with images captured by the probe 10. The communication device is known in the art and may be for example, an Ethernet or universal serial bus (USB) communication device.

In the present embodiment, the controlling computer 20 is a general purpose computer. In the alternative, the controlling computer 20 can be a microcontroller, an application specific integrated circuit, and other devices, as known to one skilled in the art, that are operative to provide the same functionality as the controlling computer 20. In the further alternative, the controlling computer 20 can be the ultrasound machine 22. Further, in the present embodiment microcontrollers 18a and 18b comprise higher power outputs to drive motors 111, 123 and 133. Microcontrollers 18a and 18b are known in the art and may be for example a Faulhaber MCDC3006 S motor controller. In the alternative, microcontrollers 18a and 18b can be a general purpose computer, an application specific integrated circuit, and other devices, as known to one skilled in the art, that are operative to provide the same functionally as microcontrollers 18a and 18b.

In the alternative, controlling computer 20 can be communicative with a microcontroller 18c and operable to transmit desired translational characteristics of the probe 10 thereto. The translational characteristics comprise the translational range and the duration of motion of the probe 10 along the longitudinal axis of the probe 10. Microcontroller 18c is communicative with the translation assembly shown in FIG. 5, and is operative to control the translational characteristics of probe 10 by driving translation motor 133 in response to information on the angular position of translation motor 133 received from translation encoder 135. Microcontroller 18c is controlled by the controlling computer 20 in a similar manner as microcontrollers 18a and 18b.

The ultrasound machine 22 receives captured images from the probe 10 as the probe 10 progresses along a planned trajectory according to operator specified vibrational and rotational characteristics. The ultrasound machine is operative to receive the actual vibrational and rotational characteristics of the probe 10 to ultrasound machine 22 to allow for synchronized data collection with images captured by the probe 10. The ultrasound machine is known in the art and may be for example an Ultrasonix Sonix machine or a BK Medical Pro Focus 2202 machine.

In the present embodiment, the vibro-elastography image acquisition system 1 comprises a number of safety features. For example, the amplitude of vibration of the probe 10 can be restricted to a maximum value. This restriction is achieved by utilizing knob 114 to lock the contact position of the wheel 109 with respect to the cam 112. Knob 114 operates to lock the sliding mount 115 of the vibration motor 111 to the slider rail 118 of the probe cradle 110, which in turn locks the contact point of the wheel 109 against the cam 112. In a further example, the force that is exerted by the probe 10 against the endocavity of a patient can be restricted to a maximum value. This restriction is achieved by selecting the leaf spring 119 such that it is not capable of providing more than a maximum restive force against probe 10. In yet a further example, the operator may immediately terminate the vibration of the probe 10 by pushing the probe 10 towards the probe cradle 110 such that the wheel 409 does not contact the cam 112. In the alternative, the motion of the motorized translation assembly 16 shown in FIG. 5 is restricted such that the translation motor 133 may not insert the probe into the patient, but may only remove the probe 10 from the patient.

In operation, the probe 10 is mounted to the apparatus 1 and inserted into the rectum of a patient. The operator then inputs a planned trajectory into the controlling computer 20 by interacting with the GUI. The planned trajectory consists of the desired vibrational characteristics and rotational characteristics of the probe 10. As discussed above, the vibrational characteristics comprise the amplitude (which cannot exceed that determined by the maximum travel of the wheel 109 against the cam 112, but which can be smaller if the vibration motor 111 does not rotate a full 360 degrees) and the frequency content of the vibrational motion of the probe 10. The rotational characteristics comprise the angular range of motion and the motion duration of the probe 10. In addition, full pre-specified motions for the vibrational and rotational motion of the probe 10 can be entered from the GUI as a sequence of time increments and the corresponding desired radial (vibration) and angular increments.

Figure 6:
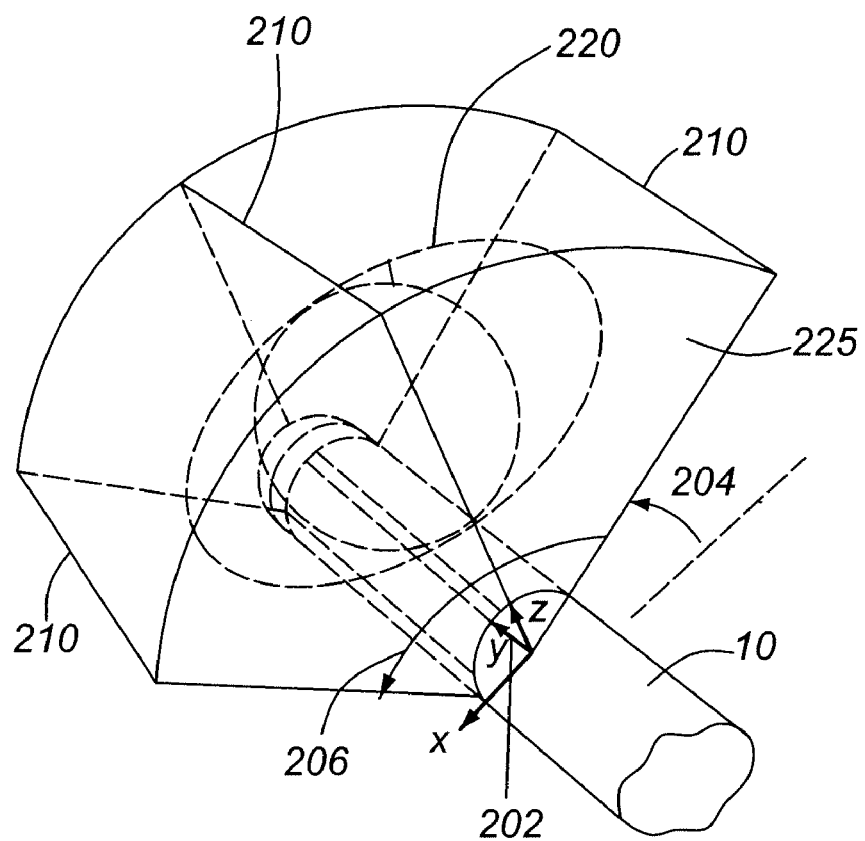
FIG. 6 is a schematic perspective view of a prostate deformed by the insertion of an ultrasound probe into the rectum of a patient.

An exemplary planned trajectory is a volume sweep of the patient's prostate. In a preferred embodiment of the present invention the volume sweep is conducted by imaging the prostate with the longitudinal transducer of the probe 10 and rotating the probe 10 about its longitudinal axis. Referring to FIG. 6, a representative drawing is provided showing a swept volume 225 acquired by capturing successive longitudinal images 210 as the probe 10 rotates between a selected rotational range between a minimum angle 204, $\theta_{min}$, and a maximum angle 206, $\theta_{max}$, about the longitudinal axis 202 of the probe 10, i.e. the Y axis. The swept volume 225 is acquired such that the entire volume of the prostate 220 is captured within the swept volume 225. In the present embodiment, this is achieved by monitoring the longitudinal image 210 as the probe 10 is inserted into the patient's rectum. The probe 10 is initially positioned within the patient's rectum such that the entire length of the prostate 220 is captured within the longitudinal image 210. In the alternative, the transverse image captured by the transverse transducer can be monitored to locate the mid-gland of the prostate 220 and ensure that the entire width of the prostate 220 is captured within the transverse image. The probe is then inserted further into the patient's rectum until the prostate 220 just disappears from the transverse image, such that the probe 10 is inserted just beyond the base of the prostate 220. In the further alternative, both the longitudinal and the transverse images can be monitored simultaneously. The probe 10 is then positioned within the patient's rectum such that the entire length of the prostate 220 is captured within the longitudinal image and the transverse image is just beyond of the base of the prostate 220. It will be obvious to those skilled in the art that many techniques exist to position the probe 10 in such a way that a desired tissue volume is acquired. Selection of these techniques depends on the training and preference of the physician involved. The above is just one out of many possible approaches.

Once the probe is positioned with respect to the prostate 220, the desired vibrational and rotational characteristics of the probe 10 are entered by the operator into the controlling computer 20 through interaction with the GUI. The vibrational characteristics are determined by initially tuning the amplitude and frequency content of vibration by assessing test images. To acquire the test images, the operator enters the desired vibrational characteristics into the controlling computer 20 and initiates the vibration of the probe 10. The captured longitudinal images 210 are then monitored on the ultrasound machine 22. The operator may adjust the vibrational characteristics of the probe 10 and its positioning within the rectum to achieve longitudinal images 210 of desired quality. For example, for patients with small prostates, the imaging depth can be reduced, allowing a higher ultrasound imaging rate and therefore a higher frequency content of the excitation signal. In some patients, the prostate motion is not necessarily in the direction of the probe compression, as the prostate slips laterally. In such patients, it may be beneficial to reduce the vibration amplitude. Larger amplitudes of vibration will lead to more significant motion of tissue that can be more easily resolved. However, if amplitudes of vibrations are too large, there will be a decrease in correlation coefficients and the tissue motion estimation may become poor. Adjustments of the probe 10 nominal location include the anterior-posterior positioning of the probe, which may affect the pre-loading pressure on the prostate while the vibration motion is exerted. Higher pressures on the rectum, and therefore on the prostate, may cause significant prostate deformation into a shape that does not correspond to the prostate shape used for treatment planning. Smaller pressures on the rectum may make coupling of the probe vibration to tissue be intermittent and which may affect the quality of acquired images. The probe 10 should make good longitudinal contact with the rectal wall in order to apply pressure to the rectum and the prostate tissue, with the nominal imaging plane when the probe 10 is at zero degree orientation (as shown in FIG. 1) coinciding with the central sagittal plane that divides the prostate into roughly symmetric left and right parts.

Next, the operator enters the desired rotational characteristics of the probe 10 into the controlling computer 20. The operator selects the scan duration, T, and a selected rotational defined by the minimum angle 204, $\theta_{min}$, and the maximum angle 206, $\theta_{max}$. The scan duration, T, is divided into N angular increments during which longitudinal images 210 are captured by the probe 10. The operator then initiates the scan. In response, the controlling computer 20 instructs microcontroller 18b to rotate the probe 10 to the minimum angle 204, $\theta_{min}$. The controlling computer 20 then instructs microcontroller 18a to vibrate the probe 10 in accordance with the desired vibrational characteristics entered by the operator. During an acquisition period, P, of T/N seconds, the probe captures a series of longitudinal images 210 which are transmitted to and stored by the ultrasound machine 22. During the same period, P, data on the actual trajectory of the probe 10 is acquired by the controlling computer 20 from microcontrollers 18a and 18b, and recorded in a synchronized manner with the series of captured longitudinal images 210. At the expiry of the acquisition period, P, the controlling computer 20 directs microcontroller 18b to rotate the probe 10 by an angular increment of $(\theta_{max}-\theta_{min})/N$. The longitudinal images 210 and actual trajectory data of the probe 210 are then recorded as described above. This process is repeated a total of N times until the probe 10 has captured the entire volume of the prostate 220 over the scan duration of T seconds.

Many tradeoffs affect the choice of sweep time, T, and angular increment $(\theta_{max}-\theta_{min})/N$. For high spatial resolution, N should be large. To characterize the low frequency response of tissue, for each longitudinal image 210, the acquisition period, P, should be at least as large as the reciprocal of the lowest frequency to be characterized. Thus, for tissue characterization down to 0.5 Hz, the acquisition period, P, should be at least 2 seconds, and the scan duration, T, should be at least 2N seconds. The imaging frame rate, $f^{US}$, of the ultrasound machine 22 determines the highest frequency of vibration, $f_{VIB}$, that the vibration assembly 12 can exert. To avoid aliasing, the imaging frame rate, $f_{US}$, should be at least twice as large as the highest frequency of vibration, $f_{VIB}$. In order to achieve higher frequencies of vibration, $f_{VIB}$, it is necessary to reduce the depth of the ultrasound imaging plane, or to reduce the width of the imaging plane, so that a single ultrasound image can be acquired in a smaller time, leading to a higher imaging frequency and therefore allowing a higher vibration frequency.

In an alternative embodiment, the volume of the prostate 220 can be captured using the transverse transducer of the probe 10 and the translation assembly 16 shown in FIG. 5. The transverse imaging plane is a sector image of the prostate 220. To scan the swept volume 225 shown in FIG. 6, the probe 10 must be incrementally retracted while capturing a series of transverse images, such that entire volume of the prostate 220 is captured. Similar to the preferred embodiment, the operator tunes the vibrational characteristics using the mid-gland image of the prostate 220. The operator then positions the transverse transducer of the probe 10 just superior to the base of the prostate 220. The operator then enters the scan duration and a number of transversal slices of the prostate 220 to be scanned and initiates the scan. The controlling computer 20 then directs microcontroller 18c to translate the probe 10 in successive intervals while the transverse images are captured and stored in ultrasound machine 22 along with data on the actual translation characteristics of the probe 10.

In the further alternative, there are many variations of this approach for longitudinal vibro-elastography image acquisition that fall within the scope of this invention. For example, a continuous motion trajectory may be imparted to the rotation of the probe 10. Also, the volume 225 may be split into smaller volumes each of which could be scanned in a shorter scan duration, T.

In the further alternative, additional adjustments may be required to the operation of the apparatus 1 as described above. For example, the depth and number of focal areas used, and the transducer center frequency may require adjustment. As well, there are further adjustments may be made to control the processing of the sequence of captured images, such as window size and overlap in window-based correlation methods.

The embodiments of the present invention described above are merely illustrative and are not to be construed as exhaustive. While the apparatus and method has been directed to imaging the mechanical properties of a prostate with the rectal cavity of the patient, the method and apparatus are also applicable to other tissue regions imaged through other endocavities, such as, the colon using a rectal probe, the ovaries using a vaginal probe, the penis using a penile probe, the upper gastro-intestinal tract using a esophageal probe, and tissue regions accessible through open wounds. Those skilled in the art may make numerous uses of, and departures from, such embodiments without departing from the spirit and the scope of the present invention. Accordingly, the scope of the present invention is not to be limited to or defined by such embodiments in any way, but rather, is defined solely by the following claims.

What is claimed is:

1. An apparatus for imaging mechanical properties of a tissue region from within an endocavity of a patient, the apparatus comprising:
    (a) an ultrasound probe insertable inside the endocavity and having a distal end contactable against the tissue region to be imaged, the distal end comprising at least one transducer array to acquire ultrasound images in an imaging plane of the transducer;
    (b) a vibration assembly translationally coupled to a proximal end of the probe and operable to vibrate the probe along a direction essentially parallel to the imaging plane, thereby causing deformational excitation of the tissue region contacted by the probe; and
    (c) a rotation assembly rotationally coupled to the vibration assembly and operable to rotate the probe and vibration assembly such that the imaging plane is rotated about a selected rotational range.

2. An apparatus as claimed in claim 1, wherein the apparatus further comprises a translation assembly translationally coupled to the probe and operable to translate the probe along the probe's longitudinal axis.

3. The apparatus of claim 2, wherein the at least one transducer array comprises a transverse array located near the probe's distal end and along a transverse axis of the probe.

4. An apparatus as claimed in claim 1, wherein the vibrational assembly is operable to vibrate the probe along a vibration axis in a vibration plane and perpendicular to a longitudinal axis of the probe.

5. An apparatus as claimed in claim 4, further comprising a cam and follower assembly translationally coupling the vibration assembly to the probe, wherein the cam rotates about an axis perpendicular to the vibration axis.

6. An apparatus as claimed in claim 5, further comprising a probe holder to which the probe is removably mounted, and wherein the follower is a wheel rotationally coupled to the probe holder, and the cam is rotationally coupled to a vibration motor of the vibration assembly.

7. An apparatus as claimed in claim 6, wherein the cam includes a first circular cylinder having a longitudinal axis perpendicular to the vibration axis such that when the wheel contacts the first cylinder there is no vibration along the vibration plane, and an adjacent second circular cylinder having a longitudinal axis at an angle from the longitudinal axis of the first cylinder such that the amplitude of vibration along the vibration plane will vary depending on the position of the wheel along the second cylinder.

8. An apparatus as claimed in claim 6, wherein the vibration assembly further comprises a probe cradle to which the vibration motor is mounted, and wherein the rotation assembly comprises a rotation motor, a drive shaft coupled to the rotation motor, and a drive gear coupled to the drive shaft and rotationally coupled to a driven gear fixed to the probe cradle.

9. An apparatus as claimed in claim 1, wherein the vibration assembly further comprises a motor, a linkage and a linear bearing assembly translationally coupling the vibration assembly to the probe.

10. An apparatus as claimed in claim 9, wherein the vibration assembly further comprises a probe cradle to which the probe is removably mounted, and wherein the linkage is rotationally coupled to the probe cradle and the motor, such that rotational motion of the motor imparts translation motion to probe cradle along the vibration plane.

11. An apparatus as claimed in claim 1, wherein the tissue region comprises at least a portion of a prostate, and the probe is an endo-rectal ultrasound probe.

12. The apparatus of claim 1, wherein the at least one transducer array comprises a linear array extending from the probe's distal end and along a longitudinal axis of the probe.

13. A method of imaging mechanical properties of a tissue region from within an endocavity of a patient, the method comprising:

(a) inserting an ultrasound probe into the endocavity of the patient and against a tissue region within the endocavity, wherein the probe comprises at least one transducer array located at a distal end of the probe to acquire ultrasound images in an imaging plane of the transducer;
(b) vibrating the probe along a direction essentially parallel to the imaging plane thereby causing deformational excitement of the tissue region contacted by the probe, wherein the vibration is caused by a vibration assembly translationally coupled to a proximal end of the probe;
(c) capturing a first series of ultrasound images of the tissue region;
(d) rotating the imaging plane vibration plane relative to the tissue region by a selected angular rotation; and
(e) capturing a second series of ultrasound images of the tissue region.

14. The method of claim 13, wherein the vibration of the probe follows a planned trajectory.

15. The method of claim 14, wherein the vibration of the probe is a filtered white noise with specified amplitude and bandwidth.

16. The method of claim 14, wherein the vibration of the probe is a sinusoid with specified amplitude and frequency.

17. The method of claim 14, wherein the rotation of the imaging plane follows a planned trajectory.

18. The method of claim 17, wherein the tissue region comprises at least a portion of a prostate and the probe is an endo-rectal ultrasound probe.

19. The method of claim 13, further comprising translating the probe and the vibration assembly along a longitudinal axis of the probe and relative to the tissue region, and capturing a further series of ultrasound images of the tissue region.

* * * * *